United States Patent
Bochner et al.

(10) Patent No.: US 7,849,859 B2
(45) Date of Patent: Dec. 14, 2010

(54) DEVICE FOR FACILITATING MEDICAL EXAMINATION

(75) Inventors: Ronnie Z. Bochner, East Brunswick, NJ (US); Andrew Lewis Wright, Kalamazoo, MI (US); Michael Stephen Rozewicz, Kalamazoo, MI (US); Kris Douglas Eager, Richland, MI (US)

(73) Assignee: Gwenventions, LLC., East Brunswick, NJ (US)

( * ) Notice: Subject to any disclaimer, the term of this patent is extended or adjusted under 35 U.S.C. 154(b) by 0 days.

(21) Appl. No.: 12/409,747

(22) Filed: Mar. 24, 2009

(65) Prior Publication Data

US 2009/0179533 A1 Jul. 16, 2009

Related U.S. Application Data

(60) Division of application No. 10/545,033, filed as application No. PCT/US2004/004431 on Feb. 13, 2004, now Pat. No. 7,694,684, which is a continuation-in-part of application No. 10/366,950, filed on Feb. 13, 2003, now Pat. No. 7,275,796.

(51) Int. Cl.
*A61G 15/00* (2006.01)
*A61B 19/02* (2006.01)
*A47B 83/00* (2006.01)
*A47B 46/00* (2006.01)

(52) U.S. Cl. .................. 128/845; 312/209; 312/235.3; 312/249.1

(58) Field of Classification Search .................. 128/845; 312/209, 235.3, 235.2, 249.1, 249.8, 249.9, 312/249.11, 249.12, 249.13; 5/640
See application file for complete search history.

(56) References Cited

U.S. PATENT DOCUMENTS 658,999 A * 10/1900 Scannell ..................... 312/209
724,125 A    3/1903 Prindle (Continued)

FOREIGN PATENT DOCUMENTS

DE       3015644    *  4/1980

(Continued)

OTHER PUBLICATIONS

International Search Report and Written Opinion dated Jun. 24, 2004, issued in International Patent Application No. PCT/US04/004431.

(Continued)

*Primary Examiner*—Patricia M Bianco
*Assistant Examiner*—Victoria Hicks
(74) *Attorney, Agent, or Firm*—Greenberg Traurig, LLP

(57) ABSTRACT

A device (10) for facilitating a medical examination includes a movable body (12) having a storage compartment (24) therein and a door member (42, 44) movably mounted to the body (12) for at least partially covering the storage compartment (24). A supporting unit (72, 72) is mounted to the body (12) for supporting a foot of a patient during the performance of a medical examination.

11 Claims, 10 Drawing Sheets

U.S. PATENT DOCUMENTS

| | | | |
|---|---|---|---|
| 804,089 | A | 11/1905 | Blanc et al. |
| 1,409,330 | A | 3/1922 | Aper |
| 1,568,498 | A | 1/1926 | Caliver |
| 1,943,282 | A | 1/1934 | Bellavia |
| 2,678,461 | A | 5/1954 | Johnson |
| 2,679,445 | A | 5/1954 | Roehm |
| 2,692,812 | A | 10/1954 | Stahl |
| 2,963,332 | A | 12/1960 | Breuning |
| 3,016,275 | A | 1/1962 | Grant |
| 3,085,842 | A | 4/1963 | Johnson |
| 3,334,951 | A | 8/1967 | Douglass, Jr. et al. |
| 3,428,383 | A | 2/1969 | Nobel |
| 3,715,148 | A | 2/1973 | Beals |
| 3,768,971 | A | 10/1973 | Fishpaw |
| 3,966,286 | A | 6/1976 | Groseclose |
| 4,114,965 | A | 9/1978 | Oye et al. |
| D250,584 | S | 12/1978 | Oye |
| 4,139,917 | A | 2/1979 | Fenwick |
| D263,995 | S | 4/1982 | Steele |
| 4,736,998 | A | 4/1988 | Wilson et al. |
| 4,790,610 | A | 12/1988 | Welch et al. |
| D304,075 | S | 10/1989 | Welch |
| 4,913,413 | A | 4/1990 | Raab |
| D332,855 | S | 1/1993 | Royse et al. |
| 5,184,601 | A | 2/1993 | Putman |
| 5,299,338 | A | 4/1994 | Foster |
| 5,399,007 | A | 3/1995 | Marconet |
| 5,405,587 | A | 4/1995 | Fernandez et al. |
| 5,518,310 | A | 5/1996 | Ellman et al. |
| 5,547,270 | A | 8/1996 | Dang |
| 5,564,803 | A | 10/1996 | McDonald et al. |
| 5,662,396 | A * | 9/1997 | Reeder et al. ............... 312/209 |
| 5,702,115 | A | 12/1997 | Pool |
| 6,022,088 | A | 2/2000 | Metzler |
| 6,619,768 | B1 | 2/2002 | Northrop et al. |
| 6,435,186 | B1 * | 8/2002 | Klemm ...................... 128/845 |
| 6,663,202 | B2 | 12/2003 | Spann |
| D512,149 | S | 11/2005 | Bochner et al. |
| 7,024,711 | B1 | 4/2006 | Stasney et al. |
| 7,275,796 | B2 | 10/2007 | Bochner et al. |
| 7,311,657 | B2 | 12/2007 | Boone et al. |
| 2004/0160147 | A1 | 8/2004 | Bochner |
| 2007/0035217 | A1 | 2/2007 | Bochner et al. |

FOREIGN PATENT DOCUMENTS

| | | |
|---|---|---|
| DE | 3015644 A1 | 10/1981 |
| GB | 403503 | 12/1933 |
| WO | WO 2004/071366 A1 | 8/2004 |

OTHER PUBLICATIONS

International Preliminary Report on Patentability dated Feb. 1, 2005, issued in International Patent Application No. PCT/US04/004431.

Non-final Office Action dated Apr. 10, 2009, issued in U.S. Appl. No. 10/545,033.

* cited by examiner

DEVICE FOR FACILITATING MEDICAL EXAMINATION

RELATED APPLICATIONS

The present application is a divisional of U.S. patent application Ser. No. 10/545,033 filed Jul. 27, 2006 now U.S. Pat. No. 7,694,684, which is a U.S. national phase application of International Patent Application No. PCT/US2004/004431 filed Feb. 13, 2004, published on Aug. 26, 2004 in the English language, which is a continuation-in-part of U.S. patent application Ser. No. 10/366,950 filed Feb. 13, 2003 now U.S. Pat. No. 7,275,796.

TECHNICAL FIELD OF THE INVENTION

The present invention relates to medical examination devices and, more particularly, to a device adapted for facilitating a medical examination.

BACKGROUND ART

Obstetric/gynecological examinations are typically performed on female patients while they lie on medical examining tables (see, e.g., U.S. Pat. No. 2,679,445 and U.S. Pat. No. 3,334,951). Prior to the performance of such an examination, the patient climbs on a medical examination table and places her feet on stirrups of the table. Due to their large size and bulkiness, these medical examination tables are not mobile. As a result, the conventional medical examination tables are not suitable for performing medical examinations on bed-bound patients.

Various movable cart-like devices have been developed for use in the medical field (see, e.g., U.S. Pat. Nos. 3,428,383, 3,715,148, 3,966,286, 4,114,965, 5,405,587, 5,564,803, 5,702,115 and 6,022,088). While these devices are adapted to carry various medical tools, equipment and/or supplies, they are not particularly suitable for performing an obstetric/gynecological examination.

DISCLOSURE OF THE INVENTION

The present invention overcomes the disadvantages and shortcomings of the prior art discussed above by providing a new and improved medical examination device. More particularly, the device includes a movable body having a storage compartment therein and at least one door member movably mounted to the body for at least partially covering the storage compartment. A supporting unit is mounted to the body for supporting a foot of a patient during the performance of a medical examination. Because of its mobility, the body can be placed adjacent a patient bed for performing a bedside medical examination.

BRIEF DESCRIPTION OF THE DRAWINGS

For a more complete understanding of the present invention, reference is made to the following detailed description of exemplary embodiments of the present invention considered in conjunction with the accompanying drawings, in which.

BEST MODE FOR CARRYING OUT THE INVENTION

Figure 1:
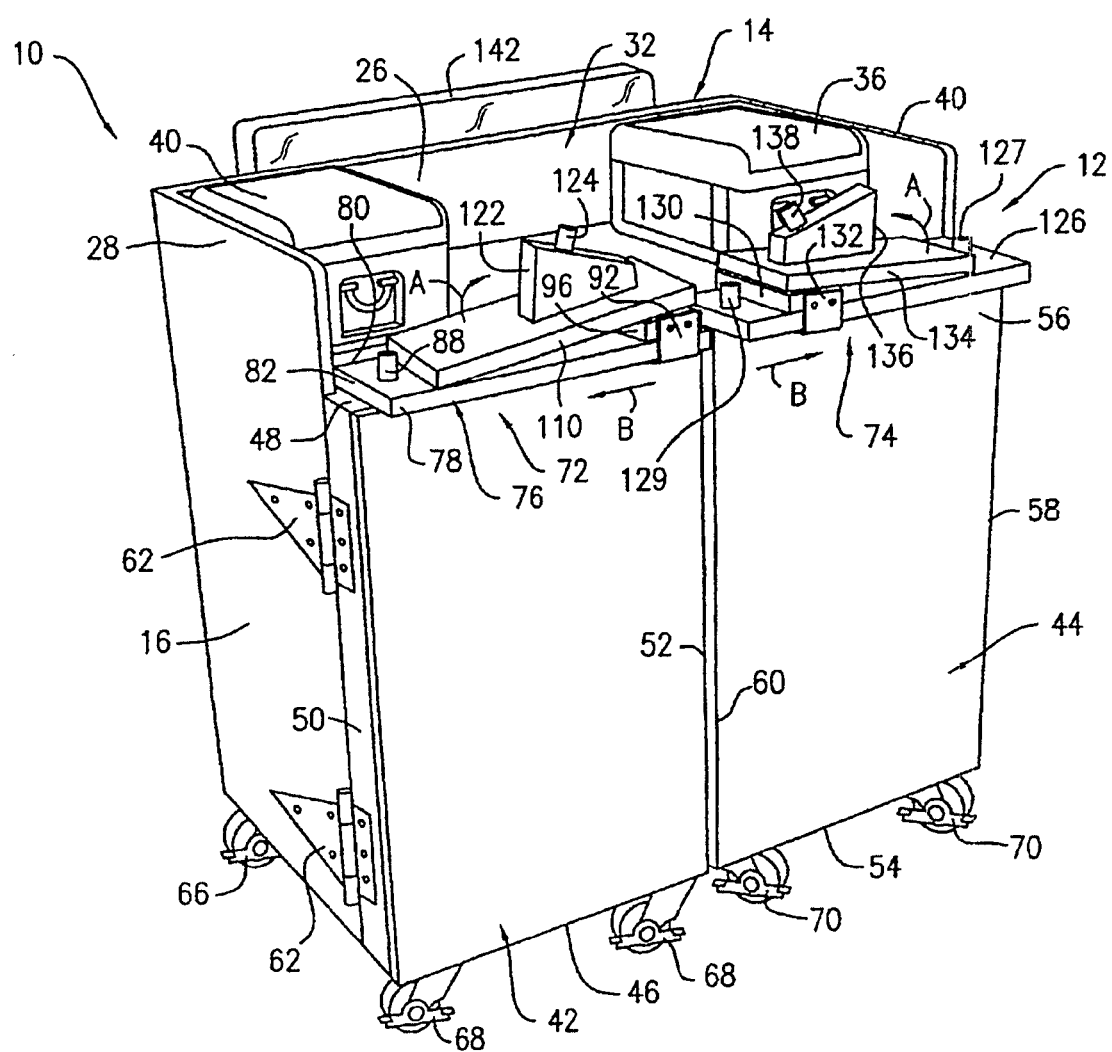
FIG. 1 is a front perspective view of a medical examination device constructed in accordance with a first embodiment of the present invention and having a pair of door panels.

FIG. 1 illustrates a medical examination device 10 constructed in accordance with a first embodiment of the present invention. More particularly, the device 10 includes a movable cart or body 12 having a rear vertical panel 14 (see FIG. 5) and a pair of lateral vertical panels 16, 18 (see FIGS. 1 and 2), both of which are attached to the rear panel 14. A lower support panel 20 (see FIG. 2) is mounted to the rear and lateral panels 14, 16, 18 adjacent lower ends thereof, while an upper support panel 22 (see FIG. 2) is attached to the rear and lateral panels 14, 16, 18 adjacent upper ends thereof. Each of the lower and upper support panels 20, 22 is oriented in a substantially horizontal manner so as to define a supporting surface for supporting various equipment utilized in the device 10. The rear panel 14, the lateral panels 16, 18 and the upper and lower support panels 20, 22 cooperate to define an interior storage space or compartment 24 (see FIG. 2) therebetween. The rear and lateral panels 14, 16, 18 also have upper portions 26, 28, 30 (see FIGS. 1, 2 and 3), respectively, all of which extend above and cooperate with the upper support panel 22 so as to define an exterior storage space 32.

Figure 2:
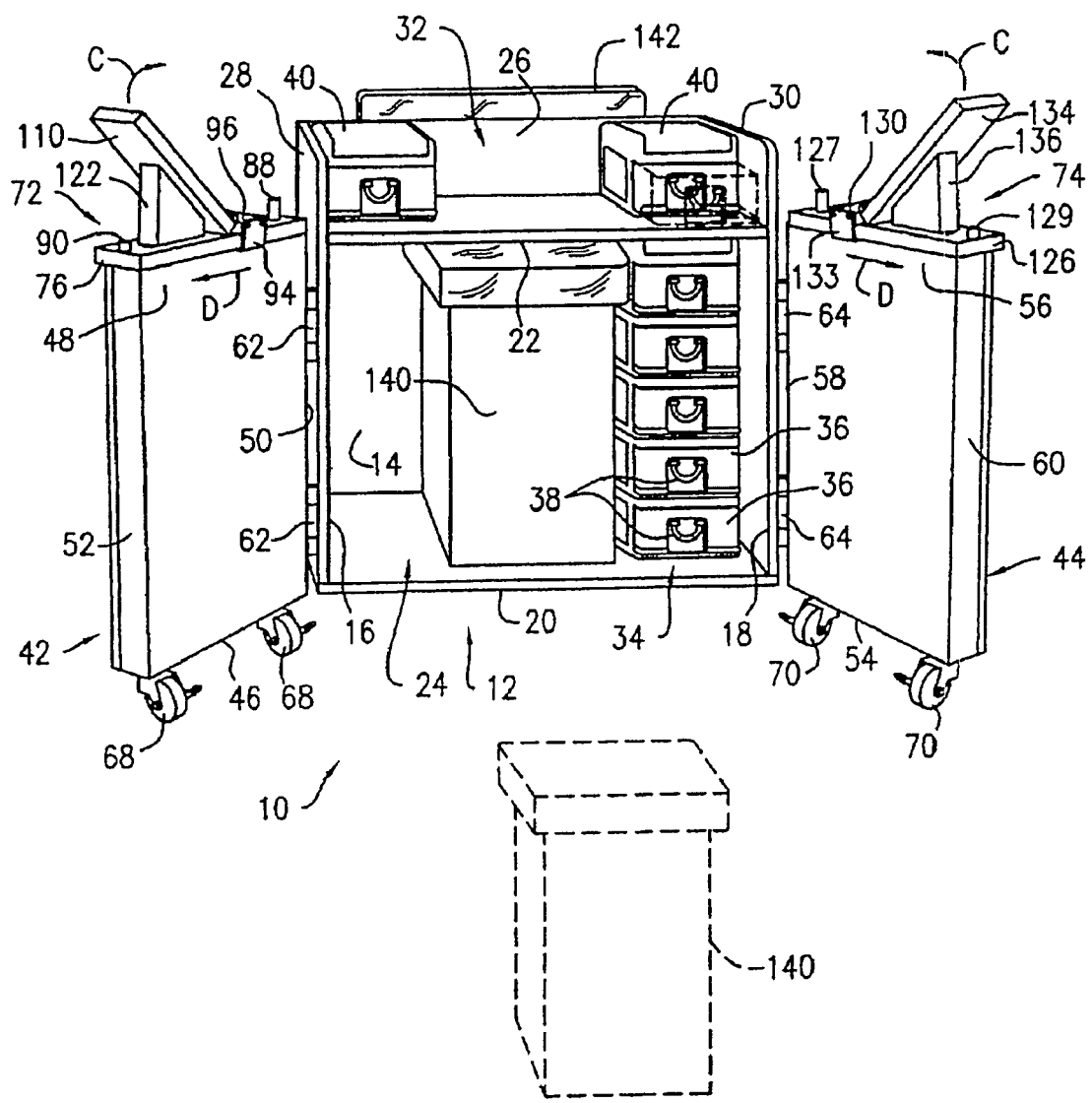
FIG. 2 is a perspective view of the medical examination device shown in FIG. 1, the door panels being illustrated in their open positions.

Referring to FIG. 2, a drawer assembly 34 is mounted in the storage space 24 adjacent the lateral panel 18. More particularly, the drawer assembly 34 includes a plurality of vertically stacked drawers 36 for storing various medical tools, supplies and other conventional items and materials (not shown) useful during the performance of a medical examination. Each of the drawers 36 has a handle 38 for use in pulling same from its closed position to its open position. Drawers 40 are also mounted in the storage space 32 (i.e., on the upper support panel 22) for providing additional storage area. Additional equipment, such as portable electric sources (e.g., batteries)

and light sources (e.g., fiber optic lights and flexible light units), can be carried onboard in the storage space 24 and/or the storage space 32.

Referring now to FIGS. 1 and 2, the cart 12 is also equipped with a pair of door panels 42, 44. The door panel 42 has lower and upper ends 46, 48 and a pair of opposing sides 50, 52, while the door panel 44 has lower and upper ends 54, 56 and a pair of opposing sides 58, 60. Hinges 62 connect the side 50 of the door panel 42 to the lateral panel 16, while hinges 64 connect the side 58 of the door panel 44 to the lateral panel 18. In this manner, each of the door panels 42, 44 is pivotable between a closed position, in which it closes off the storage space 24, and an open position, in which it is swung pivotally outwardly from the cart 12. Releasable locking mechanisms (not shown) can be provided on the door panels 42, 44 and/or the lower and upper support panels 20, 22 such that the door panels 42, 44 can be releasably maintained in their closed positions.

Figure 5:
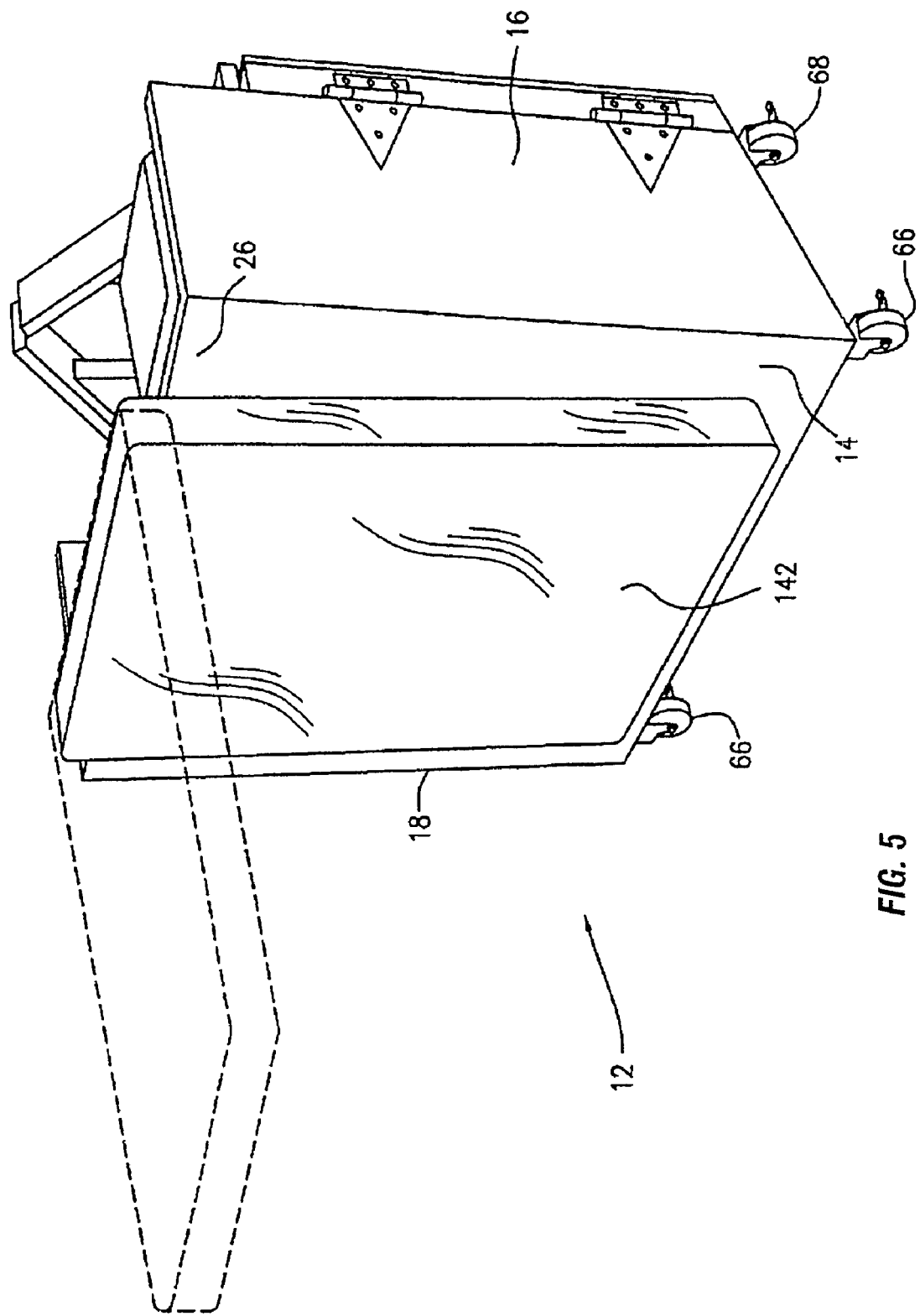
FIG. 5 is a rear perspective view of the medical examination device shown in FIGS. 1 and 2.

With reference to FIGS. 1, 2 and 5, the cart 12 includes wheels 66, 68, 70 (e.g., castor wheels) for supporting the cart 12 on a supporting surface (e.g., a floor). More particularly, the wheels 66 are attached to the lower support panel 20 adjacent the rear panel 14, while the wheels 68 and the wheels 70 are attached to the lower ends 46, 54, respectively, of the door panels 42, 44, respectively. Due to the wheels 66, 68, 70, the cart 12 can be easily moved to a desired location. The wheels 68 and the wheels 70 also facilitate the opening and closing of the door panels 42, 44, respectively.

Now referring to FIGS. 1-4, foot support assemblies 72, 74 are carried on the door panels 42, 44, respectively. More particularly, the foot support assembly 72 includes a rail member 76 fixedly attached to the upper end 48 of the door panel 42. The rail member 76, which has a pair of opposing sides 78, 80 and a pair of opposing ends 82, 84, includes a plurality of mounting holes 86 arranged in a substantially linear fashion along the longitudinal axis of the rail member 76. Retainer posts 88, 90 are mounted on the rail member 76 adjacent the ends 82, 84, respectively, for purposes to be discussed hereinafter.

Still referring to FIGS. 1-4, the foot support assembly 72 includes a pair of L-shaped brackets 92, 94 and a support block 96, which has a pair of opposing sides 98, 100 (see FIG. 4) aligned substantially with the sides 78, 80, respectively, of the rail member 76. The support block 96 is movably mounted on the rail member 76, while the brackets 92, 94 have vertical plates 102, 104, respectively, which are attached to the sides 98, 100, respectively, of the support block 96, and horizontal plates 106, 108, respectively, which are movably positioned between the rail member 76 and the upper end 48 of the door panel 42. In this manner, the brackets 92, 94 capture the rail member 76 therebetween so as to permit movement of the support block 96 along the longitudinal axis of the rail member 76.

Still referring to FIGS. 1-4, the foot support assembly 72 includes a foot rest 110 having a pair of ends 112, 114. The foot rest 110 includes a foot-resting surface 116 and a supporting surface 118 opposite the foot-resting surface 116. The end 112 of the foot rest 110 is pivotally attached to the support block 96 via a hinge 120 such that the foot rest 110 is pivotable between a folded-down position, in which the foot rest 110 is laid generally flat against the rail member 76 and hence the upper end 48 of the door panel 42 (see FIG. 1), and an unfolded position, in which the foot rest 110 extends upwardly from the rail member 76 and hence the door panel 42 in a slanted direction for supporting a patient's foot (see FIGS. 2, 3 and 5). A wedge-shaped support member 122 is attached to the supporting surface 118 of the foot rest 110 for maintaining the foot rest 110 in its unfolded position. Due to its attachment to the support block 96, the foot rest 110 is movable along the longitudinal axis of the rail member 76 conjointly with the support block 96. As a result, the foot rest 110 can be positioned in its unfolded position at one of a plurality of locations along the rail member 76 and hence the door panel 42. That is, the position of the foot rest 110 relative to the door panel 42 is adjustable. A retainer pin 124 projects from the support member 122 in a direction away from the foot rest 110. The retainer pin 124 is sized and shaped so as to be received in one of the mounting holes 86 of the rail member 76 when the foot rest 110 is in its unfolded position, thereby maintaining the foot rest 110 in its unfolded position at a preselected location along the rail member 76 and hence the door panel 42.

The foot support assembly 74 is basically identical, in construction and operation, to the foot support assembly 72. In such circumstances, the construction and operation of the foot support assembly 74 will be discussed briefly hereinafter without describing the details thereof.

Figure 3:
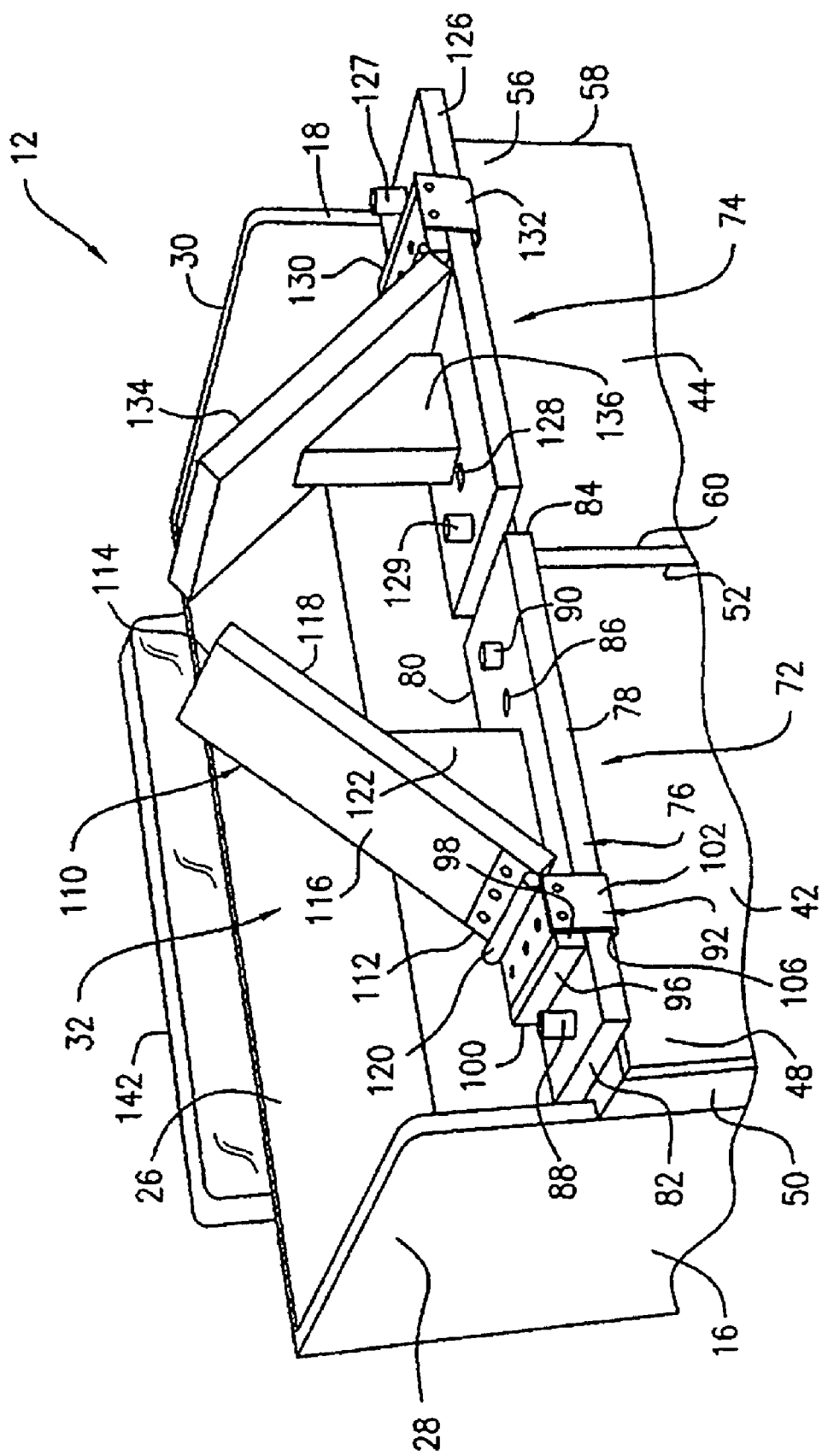
FIG. 3 is an enlarged perspective view of an upper portion of the medical examination device shown in FIGS. 1 and 2, illustrating its foot support assemblies.
Figure 4:
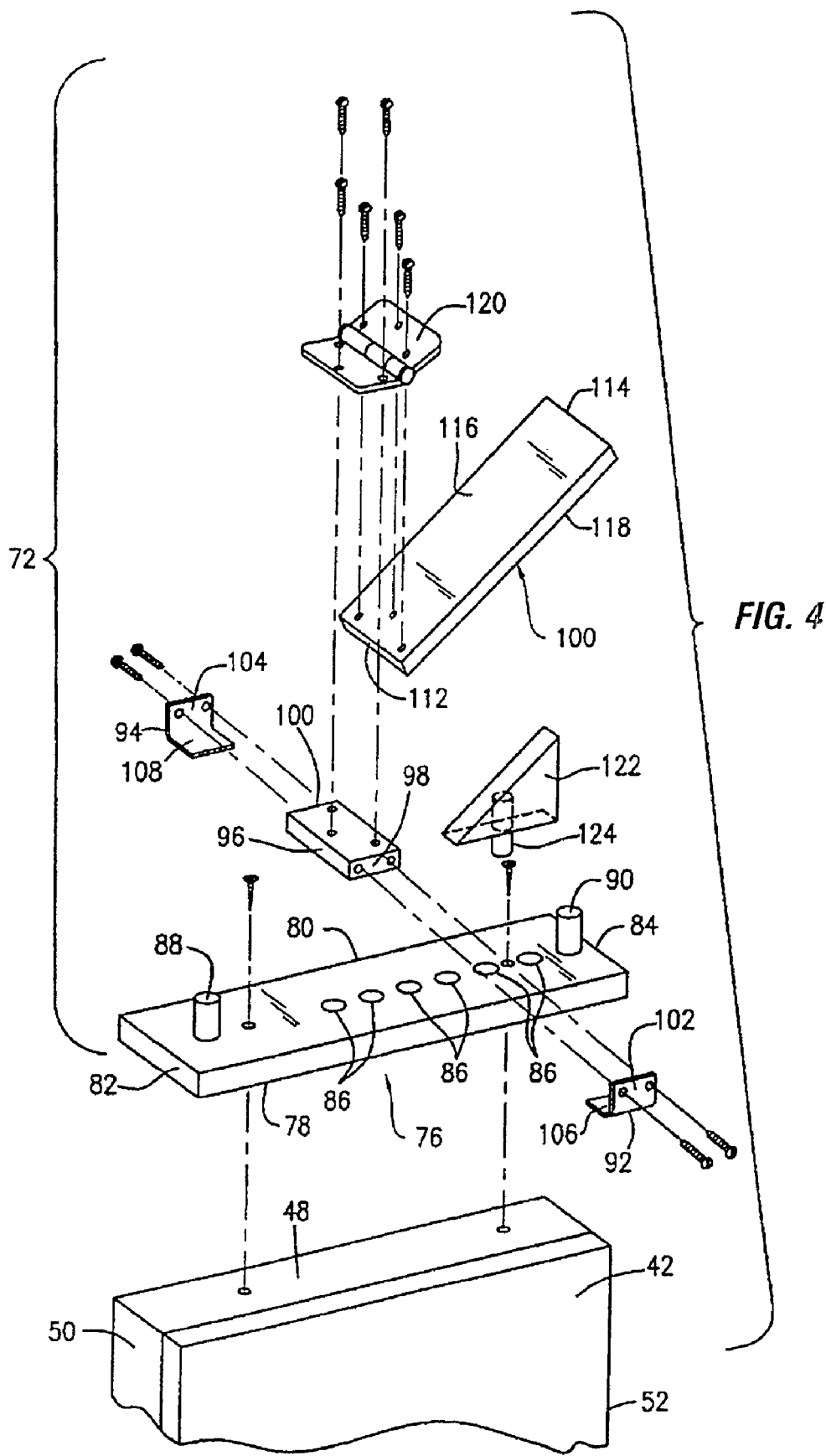
FIG. 4 is an exploded perspective view of one of the foot support assemblies shown in FIG. 3.

With reference to FIGS. 1-3, like the foot support assembly 72, the foot support assembly 74 is provided with a rail member 126 attached to the upper end 56 of the door panel 44 and having a plurality of mounting holes 128 (only one of which is shown in FIG. 3) and a pair of retainer posts 127, 129. A support block 130 is movably mounted on the rail member 126 via L-shaped brackets 132, 133, while a foot rest 134 is pivotally attached to the support block 130 such that it is pivotable between a folded-down position and an unfolded position. The foot support assembly 74 also has a support member 136, which is attached to the foot rest 134 for maintaining the foot rest 134 in its unfolded position. A retainer pin 138 projects from the support member 136 and is sized and shaped so as to be received in one of the mounting holes 128 of the rail member 126 for maintaining the foot rest 134 in its unfolded position at a predetermined location along the upper end 56 of the door panel 44.

Now referring to FIG. 2, the device 10 is also equipped with a stool (i.e., a seat member) 140. More particularly, the stool 140 is sized and shaped so as to be removably positioned in the storage space 24 of the cart 12 such that it is can be taken out from the store space 24 and used by medical personnel (e.g., a doctor) as a seat during the performance of a medical examination.

With reference to FIG. 5, a rigid support mat 142 is pivotally attached to the upper portion 26 of the rear panel 14. More particularly, the support mat 142 is sized and shaped so as to support a patient thereon during a medical examination. The support mat 142 is pivotable between an extended position, in which it extends in a substantially horizontal direction from the rear panel 14 of the cart 12 (see the broken line representation of the support mat 142 in FIG. 5), and a retracted position, in which it is oriented substantially vertically and is laid against the rear panel 14 (see the solid line representation of the support mat 142 in FIG. 5).

Figure 6:
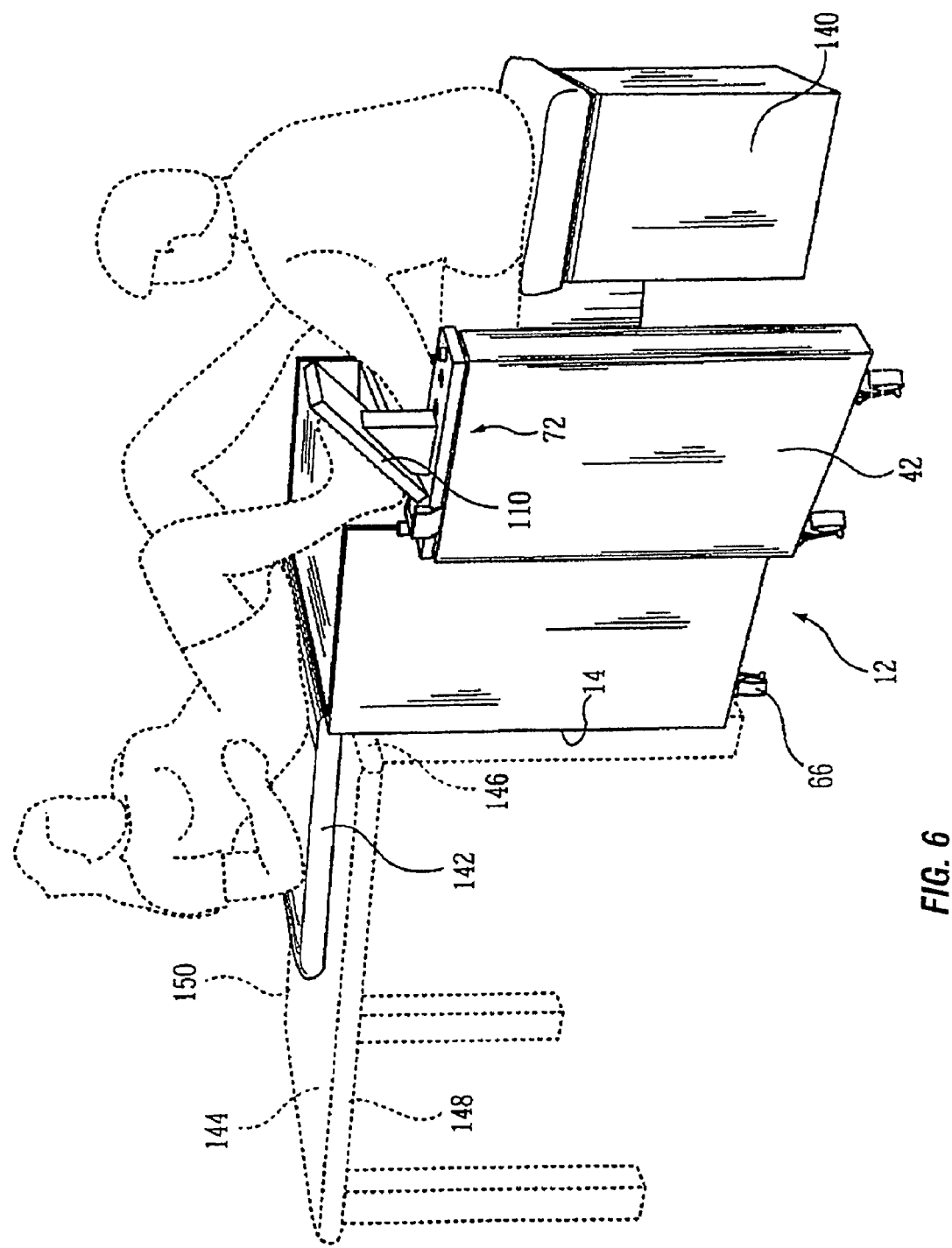
FIG. 6 is a schematic view of the medical examination device shown in FIGS. 1, 2 and 5, illustrating its use during a medical examination.

When the device 10 is not in use, it is stored away with the foot rests 110, 134 positioned in their folded-down positions and the support mat 142 positioned in its retracted position (see FIG. 1). Referring to FIG. 6, in order to perform a medical examination (e.g., an obstetric/gynecological examination) with the use of the device 10 alongside a patient bed 144 (e.g., a hospital bed) having a removable foot board (not shown) at an end 146 thereof, the foot board is removed. The cart 12 is then positioned against the end 146 of the bed 144. More particularly, with the supporting mat 142 placed and supported on the bed 144 in its extended position, the rear panel 14 of the cart 12 is positioned against the end 146 of the bed 144. Alternatively, the cart 12 can be placed against a side 148 or a side 150 of the bed 144. After properly positioning the cart 12, the wheels 66 are locked so as to prevent movement of the cart 12 relative to the bed 144. The door panels 42, 44 are then swung toward their open positions. Thereafter, the foot rests 110, 134 are pivoted from their folded-down positions toward their unfolded positions (as indicated by arrows A in FIG. 1) and are moved toward the sides 50, 58, respectively, of the door panels 42, 44, respectively, (as indicted by arrows B in FIG. 1) so as to position same at desired locations along the door panels 42, 44, respectively. In this regard, each of the retainer pins 124, 138 of the foot rests 110, 134, respectively, is inserted into a selected one of the mounting holes 86, 128 of the rail members 76, 126, thereby securing the foot rests 110, 134 to the rail members 76, 126, respectively, and hence the door panels 42, 44, respectively. A patient then places herself on the support mat 142 with her feet supported on the foot rests 110, 134 (see FIG. 6). While sitting on the stool 140, a medical personnel (e.g., a doctor) performs a medical examination (e.g., an obstetric/gynecological examination) on the patient.

After the use of the device 10, the foot rests 110, 134 are pivoted from their unfolded positions to their folded-down positions (as indicated by arrows C in FIG. 2) and are then moved toward the sides 52, 60, respectively, of the door panels 42, 44, respectively (as indicated by arrows D in FIG. 2). In this regard, the retainer posts 88, 90 of the rail member 76 maintain the support block 96 and hence the foot rest 110 on the rail member 76 (i.e., the retainer posts 88, 90 prevent the foot rest 110 from being dismounted from the rail member 76). Likewise, the retainer posts 127, 129 of the rail member 126 maintain the support block 130 and hence the foot rest 134 on the rail member 126 (i.e., the retainer posts 127, 129 prevent the foot rest 134 from being dismounted from the rail member 126).

It should be appreciated that the present invention provides numerous advantages over the prior art discussed above. For instance, because the device 10 is portable and/or mobile, medical examinations, such as obstetric and/or gynecological examinations, can be performed alongside patient beds (e.g., hospital beds). As a result, the device 10 is particularly suitable for performing medical examinations on bed-bound patients.

It should be noted that the present invention can have numerous modifications, variations and applications. For instance, the foot support assemblies 72, 74 can be replaced with conventional stirrups. Conventional stirrups can be mounted on the door panels 42, 44 such that they retract into the door panels 42, 44 when the door panels 42, 44 are closed and they pop up from the door panels 42, 44 when the door panels 42, 44 are opened. The foot support assemblies 72, 74 can also be mounted at other locations on the cart 12. In addition, the support mat 142 can be slidably mounted to the upper end of the cart 12 such that it can be positioned on the upper end of the cart 12 when it is in its retracted position. Alternatively, the support mat 142 can be eliminated or replaced with other mechanisms. Moreover, the device 10 can be used in conjunction with different types of medical devices (e.g., patient examination tables, etc.). The device 10 can also be used in performing many different types of medical examinations (e.g., gastroenterology examinations). When performing a gastroenterology examination, the cart 12 is preferably positioned along a side of a patient's bed. Further, the device 10 can be provided with other tools and equipment, such as retractable electrical cords, etc.

FIGS. 7-13 depicts a second embodiment of the present invention. Elements illustrated in FIGS. 7-13, which correspond, either identically or substantially, to the elements described above with respect to the embodiment of FIGS. 1-6, have been designated by corresponding reference numerals increased by one thousand. Unless otherwise stated and/or illustrated, the embodiment of FIGS. 7-13 is constructed and assembled in the same basic manner as the embodiment of FIGS. 1-6.

Figure 7:
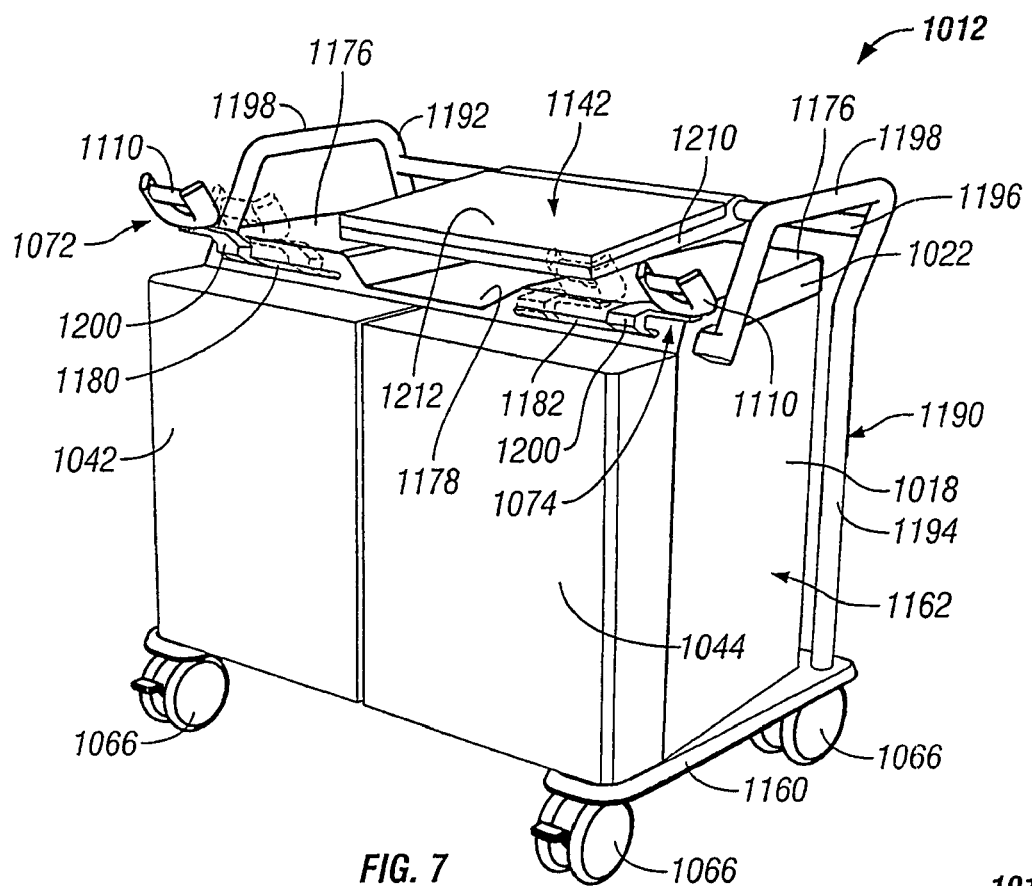
FIG. 7 is a front perspective view of a medical examination device constructed in accordance with a second embodiment of the present invention and having a pair of doors.
Figure 8:
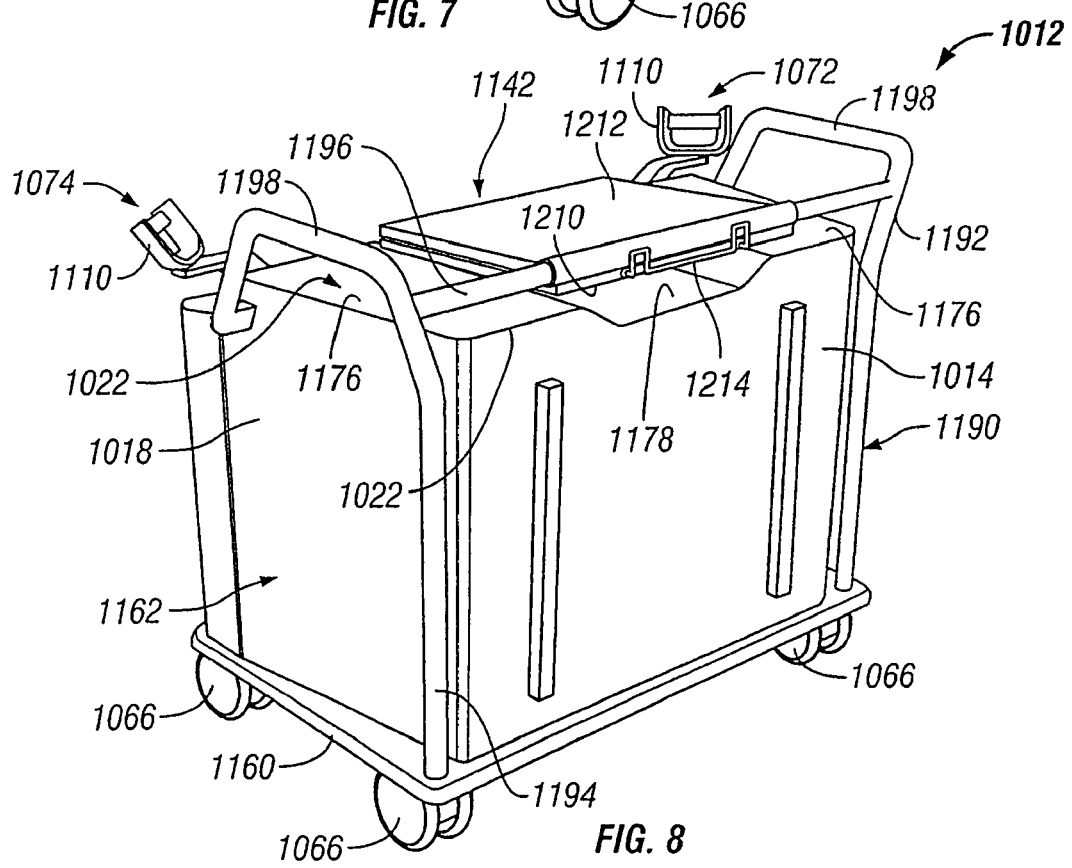
FIG. 8 is a rear perspective view of the medical examination device shown in FIG. 7.
Figure 9:
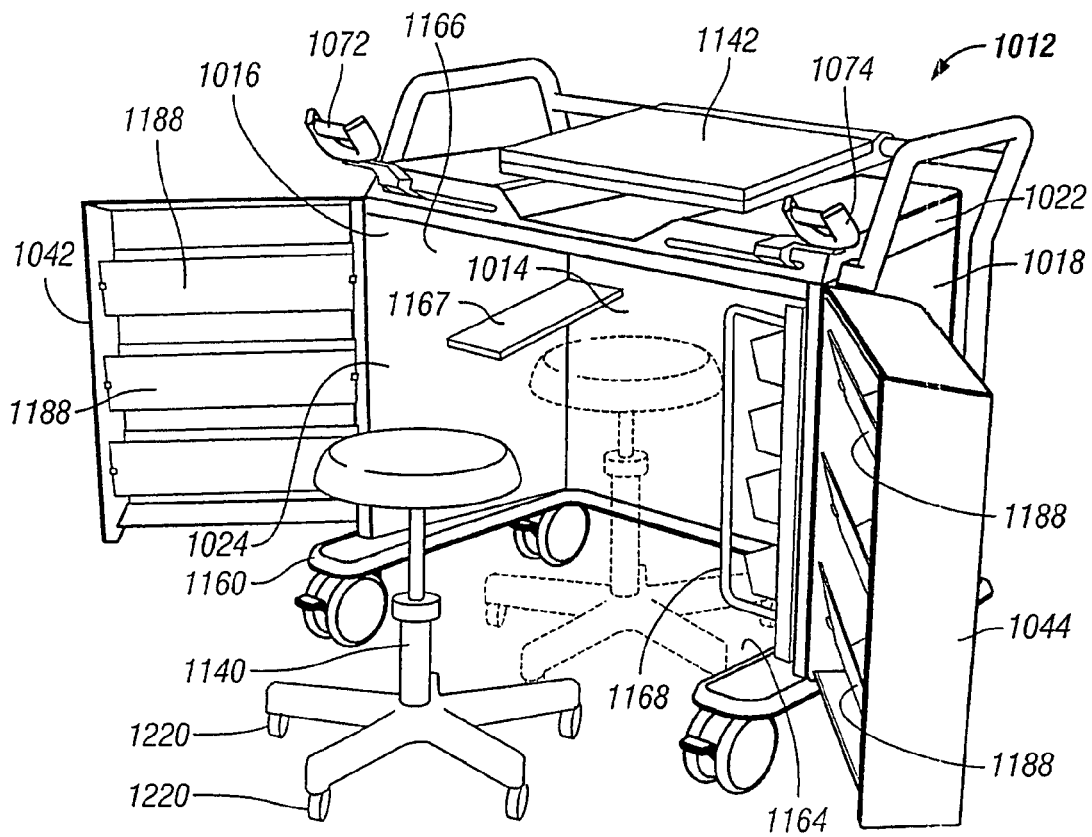
FIG. 9 is a perspective view of the medical examination device shown in FIG. 7, the doors being illustrated in their open positions.

With reference to FIGS. 7-9, there is shown a medical examination cart 1012 constructed in accordance with a second embodiment of the present invention. More particularly, the cart 1012 includes a generally U-shaped support frame 1160 and a plurality of wheels 1066 attached to the support frame 1160 such that the cart 1012 can be moved easily to a desired location. The wheels 1066 are preferably lockable caster-type wheels. Alternatively, other types of wheels can be utilized. The support frame 1160 is preferably coated with a suitable material (e.g., rubber) such that it can function as a bumper or an impact-absorber for the cart 1012.

Referring to FIGS. 7-10, the cart 1012 includes a cabinet body 1162 which can be made from any suitable materials (e.g., aluminum, stainless steel, plastic, etc.). The body 1162 is attached to and supported on the support frame 1160 such that it is movable together with the support frame 1160 and includes lateral panels 1016, 1018, a rear panel 1014 and an upper panel 1022 which cooperate to form a storage space 1024 within the body 1162. The body 1162 is also provided with an open bottom 1164 and an open front side 1166. A storage shelf 1167 is mounted to the lateral panel 1016 and the rear panel 1014 of the cart 1012, while a pull-out storage unit 1168 is mounted to the lateral panel 1018 of the cart 1012. More particularly, the storage unit 1168 includes a support panel 1170 and a plurality of storage pans 1172 affixed to the support panel 1170. The support panel 1170 is movably mounted to the lateral panel 1018 such that the storage unit 1168 is movable between a retracted position (see FIG. 9), in which the storage unit 1168 is positioned within the storage space 1024 of the cart 1012, and an extended position (see FIG. 10), in which the storage unit 1168 projects outwardly from the storage space 1024. Each of the storage pans 1172 is sized and shaped so as to receive and hold various medical equipment, tools and/or supplies. A handle 1174 is attached to the support panel 1170 so as to facilitate the movement of the storage unit 1168 between its extended and retracted positions.

Figure 12:
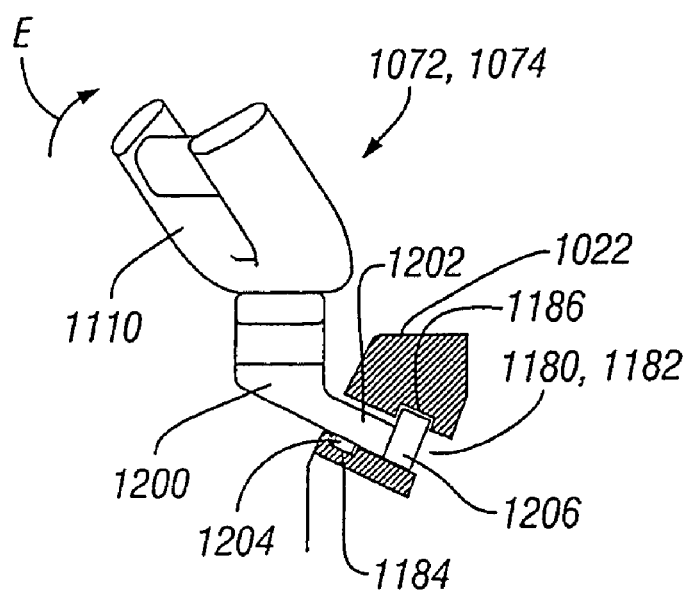
FIG. 12 is a cross-sectional view of a mounting mechanism which is utilized in the medical examination device shown in FIG. 7 for movably mounting a foot support assembly thereto.
Figure 13:
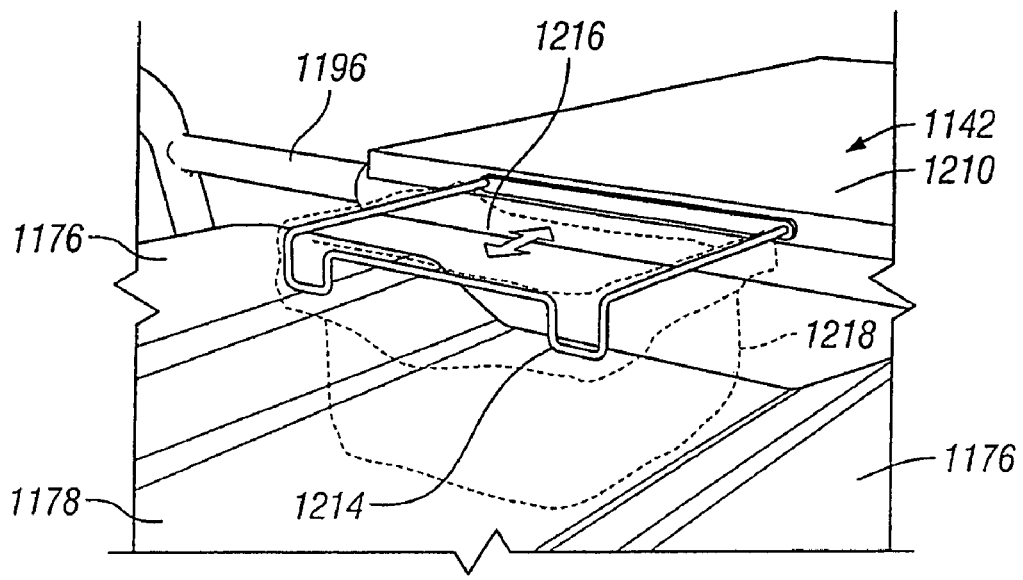
FIG. 13 is a perspective view of a rack which is utilized in the medical examination device shown in FIG. 7.

With reference to FIGS. 7, 8 and 13, the upper panel 1022 of the cart 1012 includes a pair of elevated areas 1176 and a recessed area 1178 positioned between the elevated areas 1176. The upper panel 1022 also includes a pair of slots 1180, 1182, each of which extends in a lateral direction (i.e., in a direction substantially parallel to a longitudinal axis of the cart 1012). Each of the slots 1180, 1182 includes a lower groove 1184 and an upper groove 1186 (see FIG. 12) extending in the lateral direction for purposes to be discussed hereinafter.

Figure 10:
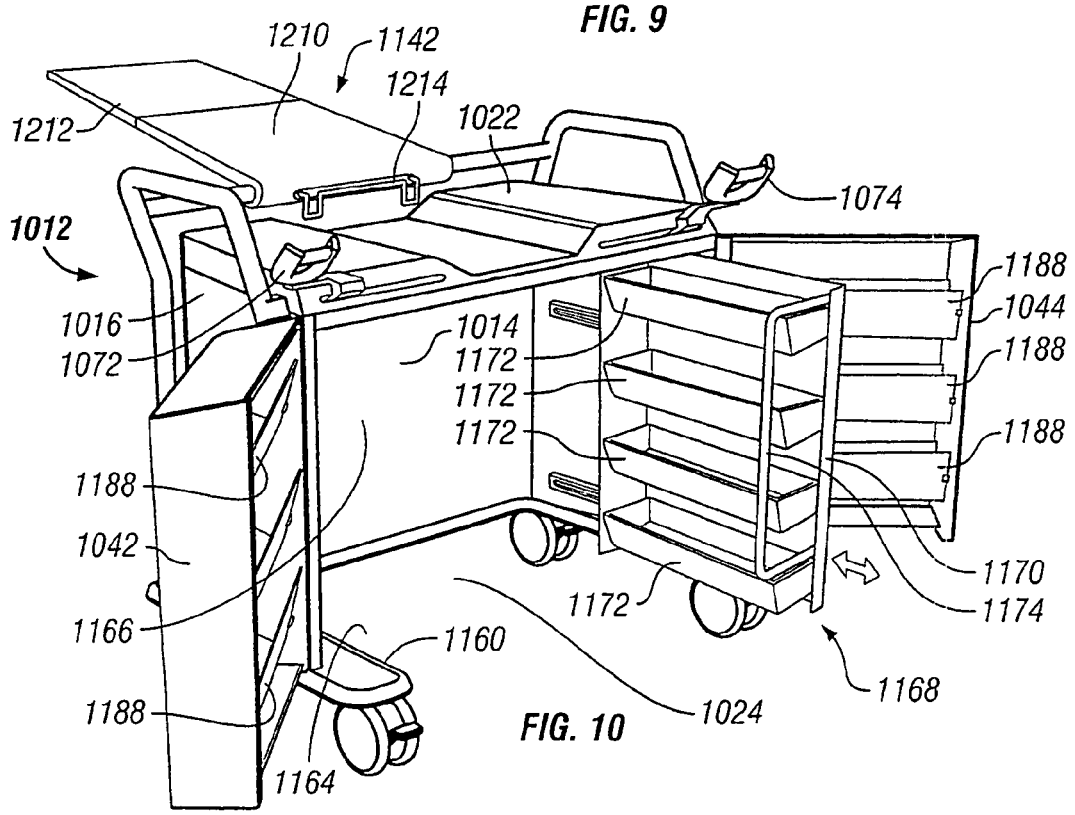
FIG. 10 is a perspective view of the medical examination device shown in FIG. 7 and having a storage pan unit, which is illustrated therein its extended position.
Figure 11:
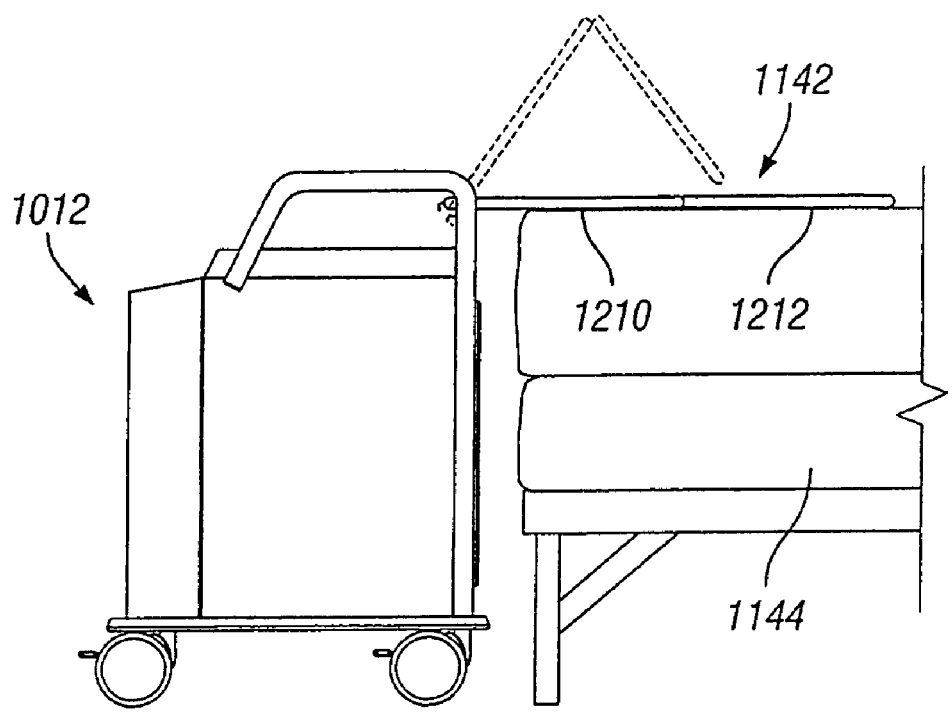
FIG. 11 is a schematic view of the medical examination device shown in FIG. 7, illustrating the movement of its support mat from a folded position to an extended position.

Referring now to FIGS. 7, 9 and 10, the cart 1012 is provided with doors 1042, 1044 pivotally mounted to the lateral panels 1016, 1018, respectively, so as to close off the open front side 1166 of the cart 1012 when they are positioned in their closed positions (see FIG. 7). When the doors 1042, 1044 are pivoted to their open positions (see FIGS. 9 and 10) from their closed positions, the storage space 1024 of the cart 1012 is accessible through the open front side 1166. Storage pans 1188 are mounted to each of the doors 1042, 1044 so as to receive and hold various medical equipment, tools, supplies, etc. Each of the doors 1042, 1044 can be constructed from any suitable material, such as aluminum, stainless steel and plastic.

The cart 1012 also includes a tube assembly 1190 (see FIGS. 7 and 8) having a pair of lateral members 1192, 1194 and a transverse member 1196 spanning between the lateral members 1192, 1194. More particularly, the lateral member 1192 is attached to the support frame 1160 and the lateral side 1016, while the lateral member 1194 is attached to the support frame 1160 and the lateral side 1018. Each of the lateral members 1192, 1194 includes a horizontal section 1198 which functions as a handle when the cart 1012 is pulled or pushed by medical personnel. The tube assembly 1190 can be made from any suitable material (e.g., aluminum, stainless steel, plastic, etc.).

With reference to FIGS. 7, 8 and 12, foot support assemblies 1072, 1074 are movably attached to the cart 1012. Each of the foot support assemblies 1072, 1074 includes a supporting bracket 1200 and a stirrup 1110 pivotally or rotatably supported on the bracket 1200. Each of the brackets 1200 has a mounting end 1202 (see FIG. 12) positioned in a corresponding one of the slots 1180, 1182 such that its corresponding foot support assembly 1072, 1074 is movable in the lateral direction. More particularly, each of the ends 1202 of the brackets 1200 is provided with a pair of gliders 1204, 1206, which are received in the grooves 1184, 1186, respectively, of a corresponding one of the slots 1180, 1182. The gliders 1204, 1206 of each of the brackets 1200 are movable in the grooves 1184, 1186, respectively, of a corresponding one of the slots 1180, 1182 such that each of the foot support assemblies 1072, 1074 can be moved laterally between an outward position (see the solid line representation of the foot support assemblies 1072, 1074 in FIG. 7) and an inward position (see the broken line representation of the foot support assemblies 1072, 1074 in FIG. 7). As a result, each of the foot support assemblies 1072, 1074 can be set at any one of an infinite number of positions between its inward and outward positions so as to accommodate different patients.

Referring to FIG. 12, each of the gliders 1204, 1206 of the brackets 1200 can be made from any suitable materials, such as nylon, to facilitate its lateral movement in a corresponding one of the grooves 1184, 1186. Due to the weight of the stirrups 1110, the foot support assemblies 1072, 1074 tilt downwardly, causing the gliders 1204, 1206 to engage inner surfaces defining the corresponding grooves 1184, 1186 and thereby automatically locking the foot support assemblies 1072, 1074 in place. Each of the foot support assemblies 1072, 1074 can be released and moved laterally from its locked position by tilting same in an upward direction (as indicated by arrow E in FIG. 12).

With reference to FIGS. 7, 8, 10 and 11, the cart 1012 is equipped with a support mat 1142 having a pair of sections 1210, 1212. More particularly, the section 1210 is pivotally attached to the transverse member 1196 of the tube assembly 1190, while the section 1212 is pivotally attached to the section 1210. In this manner, the mat 1142 can be oriented in a folded position, in which the mat 1142 is folded upon itself and placed on the upper panel 1022 of the cart 1012 (see FIGS. 7-9), or in an extended or unfolded position, in which it projects outwardly from the cart 1012 (see FIGS. 10 and 11). The mat 1142 is sized and shaped such that, when it is oriented in its folded position, it does not protrude outwardly from the cart 1012. In use, the mat 1142 is positioned in its unfolded position and is placed on a hospital/patient bed 1144 (see FIG. 11) such that it can be sat on by a patient.

Now referring to FIGS. 8, 10 and 13, the mat 1142 is provided with a rack 1214. More particularly, the rack 1214 is movable between a retracted position, in which it is retracted into the section 1210 of the mat 1142 (see FIGS. 8 and 10), and an extended position, in which it extends outwardly in a forward direction from the section 1210 (see FIG. 13). The rack 1214 has an opening 1216 such that a disposable bag 1218 can be mounted from the rack 1214. During the performance of a medical procedure (e.g., an emergency delivery/childbirth or surgery), waste materials, such as bodily fluid and tissues discharging from the patient, can be disposed into the disposable bag 1218. In this regard, the disposable bag 1218 can be supported by the recessed area 1178 (see FIG. 13) of the cart 1012 and is retained between the elevated areas 1176.

Referring back to FIG. 9, a stool 1140 is provided in conjunction with the cart 1012. More particularly, the stool 1140 is provided with wheels 1220 such that the stool 1140 can be moved easily to a desired location. The storage space 1024 is sized and shaped such that the stool 1140 can be received in the storage space 1024 (see the broken line representation of the stool 1140 in FIG. 9). In this manner, the stool 1140 can be stowed in the storage space 1024 and be moved to a desired location together with the cart 1012.

In use, the cart 1012 is placed adjacent to the bed 1144 (see FIG. 11), and the mat 1142 is unfolded from its folded position to its extended position and placed on the bed 1144. If desired, the rack 1214 can be pulled out from the mat 1142 so that the disposable bag 1218 can be mounted therefrom. The foot support assemblies 1072, 1074 can also be moved to desired lateral locations to comfortably support the patient's feet during the performance of a medical examination or procedure.

Figure 14:
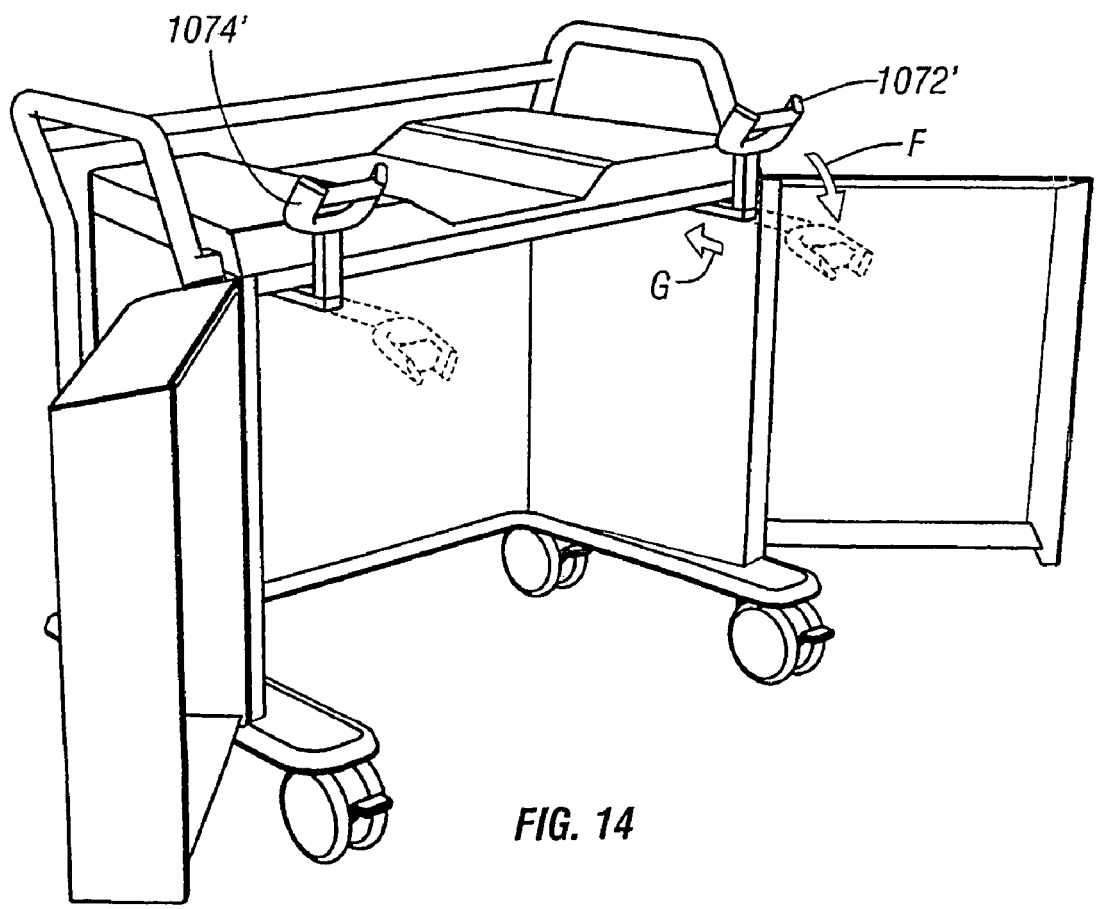
FIG. 14 is a perspective view of the medical examination device shown in FIG. 7, illustrating modified foot support assemblies.

It should be noted that the cart 1012 can have numerous modifications and variations. For instance, the foot support assemblies 1072, 1074 can be mounted on the cart 1012 at different locations. In addition, the foot support assemblies 1072, 1074 can be provided with different mechanisms for mounting same to the cart 1012. For instance, the cart 1012 can be provided with foot support assemblies 1072', 1074' (see FIG. 14) which are completely retractable into the storage space 1024 (as illustrated by arrows F and G in FIG. 14).

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

The invention claimed is:

1. A device for facilitating a medical examination, comprising a movable cart having a front side, a rear side opposite said front side, a first lateral side, a second lateral side opposite said first lateral side, a top, and a bottom opposite said top, said cart having a substantially unobstructed storage compartment therein said storage compartment extending from said first lateral side to said second lateral side and from said top to said bottom, said first and second lateral sides are spaced from one another along a longitudinal axis of said cart, and said cart having at least one door member pivotally mounted to said cart adjacent said front side for at least partially covering said storage compartment; a first slot having a first upper groove with an inner surface and a first lower groove with an inner surface, and a second slot having a second upper groove with an inner surface and a second lower groove with an inner surface; and first and second foot supports projecting generally upwardly from said cart adjacent said front side thereof, each of said first and second foot supports being sized and shaped so as to support one foot of a patient during the performance of a medical examination, said first foot support includes a first bracket, and said second foot support includes a second bracket, said first and second brackets are movable laterally along said longitudinal axis, said first bracket includes a first end movably mounted in said first slot for supporting said first foot support therefrom, and said second bracket includes a second end movably mounted in said second slot for supporting said second foot support therefrom, said first end of said first bracket including a first pair of gliders, one of which is movably mounted in said first upper groove of said first slot and the other of which is movably mounted in said first lower groove of said first slot, said second end of said second bracket including a second pair of gliders, one of which is movably mounted in said second upper groove of said second slot and the other of which is movably mounted in said second lower groove of said first slot, said first foot support being movable between a locked position, in which said first foot support is tilted in a downward direction to cause one of said first pair of gliders to engage said inner surface of said first upper groove and the other of said first pair of gliders to engage said inner surface of said first lower groove, and a released position, in which said first foot support is titled in an upward direction opposite the first direction to cause each of said first pair of gliders to disengage said corresponding inner surfaces of said first upper groove and said first lower groove, and said second foot support being movable between a locked position, in which said second foot support is tilted in a downward direction to cause one of said second pair of gliders to engage said inner surface of said second upper groove and the other of said second pair of gliders to engage said inner surface of said second lower groove, and a released position, in which said second foot support is titled in an upward direction opposite the third direction to cause each of said second pair of gliders to disengage said corresponding inner surfaces of said second upper groove and said second lower groove.

2. The device of claim 1, further comprising a support member carried by said cart and sized and shaped so as to support a patient thereon during the performance of a medical examination.

3. The device of claim 2, wherein said support member is pivotally attached to said rear side of said cart such that said support member is movable between an extended position, in which said support member extends outwardly from said rear side, and a retracted position, in which said support member does not extend substantially outwardly from said rear side.

4. The device of claim 3, wherein said support member includes a first section, which is pivotally attached to said cart, and a second section, which is pivotally attached to said first section.

5. The device of claim 4, wherein said first section has first and second ends, said first end being pivotally attached to said cart such that said first section is positioned on said top of said cart when said support member is in its said retracted position; and wherein said second section has a third end, said third end being pivotally attached to said second end of said first section such that said second section is positioned on said first section when said support member is in its said retracted position.

6. The device of claim 2, wherein said support member includes a foldable mat movably attached to said rear side of said cart.

7. The device of claim 1, further comprising a seat member sized and shaped so as to be positioned in said storage compartment, said seat member being removable from said storage compartment such that said seat member can be positioned in a spaced relationship relative to said cart.

8. The device of claim 7, wherein said bottom of said cart is open to a floor surface supporting said cart, said seat member being supported directly on the floor surface when said seat member is positioned in said storage compartment.

9. The device of claim 8, further comprising a substantially U-shaped support frame, laid bottom of said cart including an opening therein, said support frame defining said opening of said bottom.

10. The device of claim 1, wherein said first foot support includes a first stirrup mounted to said first bracket; and wherein said second foot support includes a second stirrup mounted to said second bracket.

11. The device of claim 1, wherein each of said first and second foot supports is retractable completely into said storage compartment.

\* \* \* \* \*